United States Patent [19]
Woodcock et al.

[11] Patent Number: 5,540,096
[45] Date of Patent: Jul. 30, 1996

[54] METHOD FOR THE NON-DESTRUCTIVE EVALUATION OF PRESTRESSED CONCRETE STRUCTURES

[75] Inventors: Michael W. Woodcock, Laurel, Md.; Richard J. Holt, Westborough, Mass.

[73] Assignee: Washington Suburban Sanitary Commission, Laurel, Md.

[21] Appl. No.: 257,322

[22] Filed: Jun. 7, 1994

[51] Int. Cl.$^6$ ................................................. G01N 29/04
[52] U.S. Cl. ........................... 73/579; 73/592; 73/1 DV
[58] Field of Search ................................. 73/1 DV, 579, 73/582, 592, 600, 622, 623; 364/507, 508, 571.02; 367/13, 14

[56] References Cited

U.S. PATENT DOCUMENTS

| | | | |
|---|---|---|---|
| 4,285,243 | 8/1981 | Collingwood | 73/623 |
| 4,435,984 | 3/1984 | Gruber | 73/1 DV |
| 4,641,529 | 2/1987 | Lorenzi et al. | 73/601 |
| 4,998,208 | 3/1991 | Buhrow et al. | 364/512 |
| 5,090,259 | 2/1992 | Shishido et al. | 73/866.5 |
| 5,095,465 | 3/1992 | Stokoe, II | 367/14 |
| 5,257,544 | 11/1993 | Khuri-Yakub | 73/597 |

*Primary Examiner*—Hezron E. Williams
*Assistant Examiner*—Christine K. Oda
*Attorney, Agent, or Firm*—Millen, White, Zelano & Branigan, P.C.

[57] ABSTRACT

A method for detecting degraded pipe used in water mains monitors detected sound waves and observes the characteristics of those waves. Water main pipes have coiled therearound highly tensioned steel wire which holds the concrete comprising the pipes in compression. When the steel wire is corroded by water seeping through mortar encapsulating the pipe, the steel wire eventually ruptures, thus relieving compression in the concrete adjacent the rupture. Sonic and ultrasonic sound waves traversing the concrete of pipes have different characteristics for pipe in good condition as compared to the characteristics of sound waves traversing pipe in poor condition due to decompression and/or other causes. The sound waves in pipe in poor condition travel slower with shear waves having less amplitude and reflections occurring at later times. In addition, the frequency domain characteristics of pipe in poor condition differ from the frequency domain characteristics of pipe in good condition. In pipe in poor condition, resonance occurs at lower frequencies than pipe in good condition. In addition, a drum head effect is apparent in pipe in poor condition, which drum head effect does not occur with pipe in good condition.

11 Claims, 5 Drawing Sheets

5,540,096

METHOD FOR THE NON-DESTRUCTIVE EVALUATION OF PRESTRESSED CONCRETE STRUCTURES

FIELD OF THE INVENTION

This invention is directed to methods for the non-destructive evaluation of prestressed or reinforced concrete structures. More particularly, this invention is directed to methods for the non-destructive evaluation of prestressed concrete structures such as those of prestressed concrete cylinder pipe (PCCP).

BACKGROUND OF THE INVENTION

Large pipes, known as water mains, deliver water for distribution through smaller diameter mains and pipes to municipal communities. These large mains have diameters typically in the range of 16 to 144 inches, and for special projects up to 252 inches, and convey water under pressure so that water can be eventually delivered under pressure to thousands of faucets and other outlets.

As with other components of infrastructures, water mains are subject to both environmental and use stress, which over time degrade mains to the point of failure. When a water main fails, the results are often catastrophic since millions of gallons of water carry away soil and undermine adjacent surface structures such as roads and, on occasion, buildings. Accordingly, in addition to loss of potable water, which is not inexpensive to accumulate, there is the expense of repairing the mains, filling the holes left by the breaks in the mains and repairing adjacent structures. Repairing, rebuilding and making restitution of damage caused by vast volumes of released waters from a single failure can cost in the range of a few hundred thousand to millions of dollars. As the infrastructure ages, the number of failures occur at an increasing rate, costing municipalities hundreds of millions of dollars every year.

Since water mains are buried, there is currently no effective way to monitor the condition of water main walls from the surface of the ground. While seismic systems can perhaps reveal the location and material composition of a pipe, seismic systems are not sensitive enough to reveal the condition of pipe walls. Radar is also now being used to penetrate the earth's surface and reveal phenomenon beneath the surface but, like sonar, radar signals cannot reveal wall structure. In addition, the soil above a water main can vary composition and can contain other structures such as rocks and assorted debris which interference with the consistency of reflected signals. Since with PCCP there is no leak before a break, which is sudden explosive burst, leak detection technology cannot be used to identify risk conditions that may be developing.

In that current technology has no means for adequately predicting failure by evaluating pipe structure from the surface of the ground, attempts have been made to predict pipe failure by making an evaluation from within the pipe. To date, no effective method or apparatus for doing this has emerged.

The only indicator of eventual pipe failure is the occurrence of a longitudinal crack which appears during the last stages of a progression to pipe failure. This longitudinal crack occurs on the inner surface of the pipe wall and coincides with approximately a breakage of 40 wire turns at the end of the pipe and 100 wire turns mid-length of the pipe. Since there is only a short period of time between the appearance of this longitudinal crack and failure, the occurrence of the crack may be only hours, weeks or perhaps several months before the break. This warning is inadequate in that it conveys nothing about the status of adjoining pipes which may have damage which has progressed to a stage just prior to the appearance of a visual crack.

In view of the aforementioned considerations, there is a need for an arrangement which can evaluate the structure of a water main and predict if, and with some degree of reliability, when a failure will occur, so risk management strategies can be put into place.

SUMMARY OF THE INVENTION

It is a feature of the present invention to provide a new and improved method of evaluating the condition of prestressed or reinforced concrete structures.

In a more specific aspect, it is a feature of the present invention to provide a method of evaluating the condition of stressed concrete structures such as prestressed concrete cylinder pipe used, for example, in water mains.

In view of these features, and other features, the present invention is directed to a method useful in evaluating the condition of prestressed concrete cylinder pipe wherein the pipe comprises either a lined steel cylinder, or an embedded steel cylinder with at least an inner concrete layer, a prestressed strand layer disposed around the steel cylinder or a concrete layer and an outer mortar layer disposed over the prestressed strand layer. In accordance with the method, frequency domain characteristics and velocity characteristics of compressional and shear sound waves are generated from an impact signal applied to the inner surface of the concrete layer of a pipe in good condition. Frequency domain characteristics and velocity characteristics of reflected compressional and shear sound waves are then generated by applying an impact signal of the same intensity to the inner surface of the concrete layer of the pipe being evaluated. The detected signals of the pipe being evaluated are then compared to the detected signals of the pipe known to be in good condition in order to determine if a rupture has occurred in the prestressed strand layer.

In a more specific aspect, the pipe under evaluation utilizes prestressed steel wire as the strand material and includes a steel membrane between a concrete core layer and liner layer of the inner layer of concrete.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
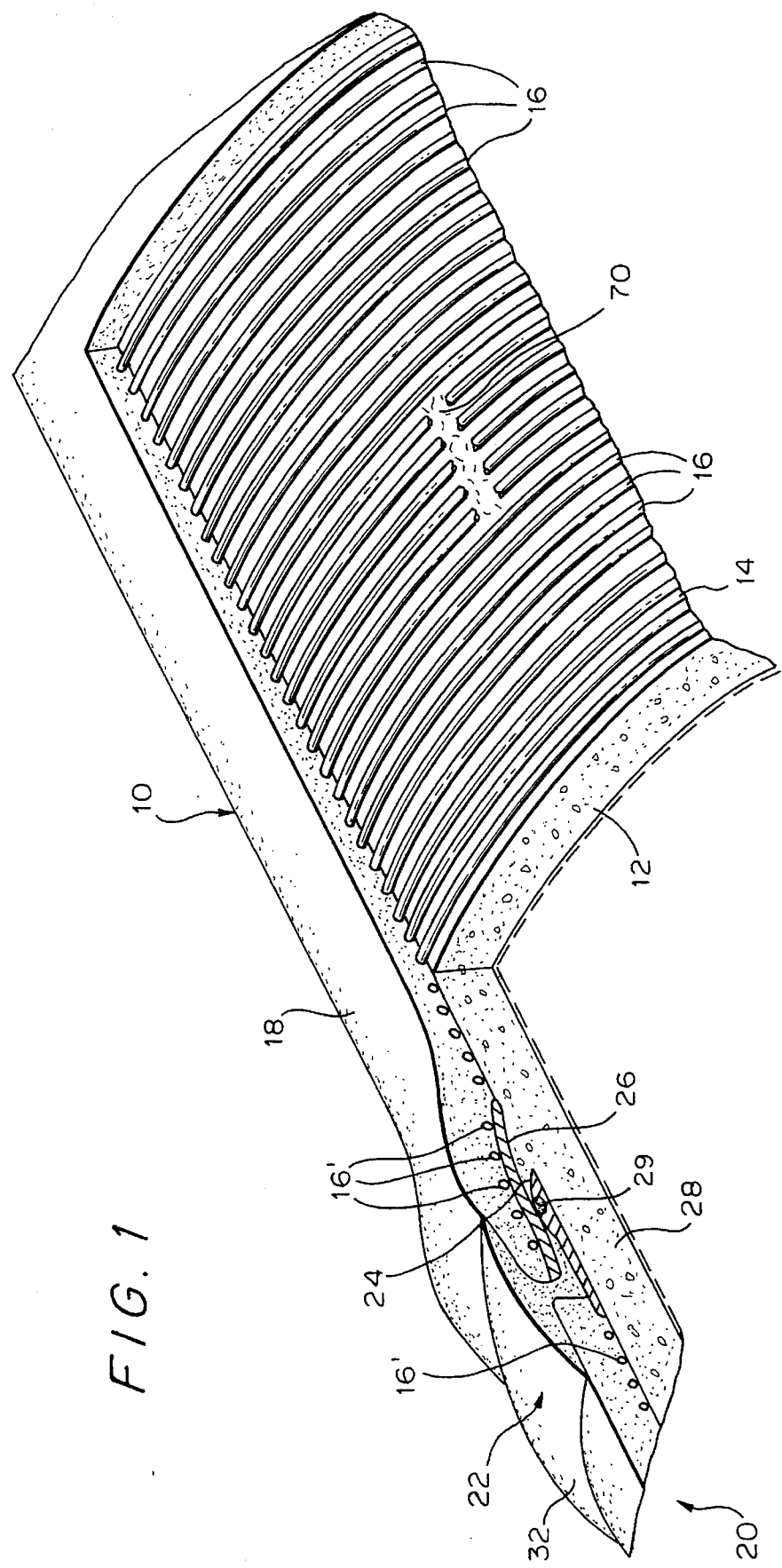
FIG. 1 is a perspective view with portions in cross-section illustrating a pipe of a first configuration.

Referring now to FIG. 1, a PCCP pipe 10 of a first embodiment known as a lined cylinder pipe is shown. The pipe 10 includes a inner layer of concrete 12; a layer of steel 14 which forms what is known as a steel membrane; a strand layer 16 comprised of coiled steel wire and finally a layer of mortar 18 which envelopes the steel reinforcing wires over areas thereof which do not abut the steel membrane.

The PCCP pipe 10 is coupled to a second similarly configured PCCP pipe 20 by a joint 22. At the joint 22, there is an annular lip 24 which extends from the pipe 10. The lip 24 has a gasket 26 on the underside thereof around which steel reinforcing wire 16' is wrapped over steel cylinder 14. The lip 24 also overlies a male end 28 of the PCCP pipe 20 with the gasket 26 on the lip abutting a gasket 29 on the male end of the pipe 20. The joint is then covered by a layer of sealing mortar 32.

Figure 2:
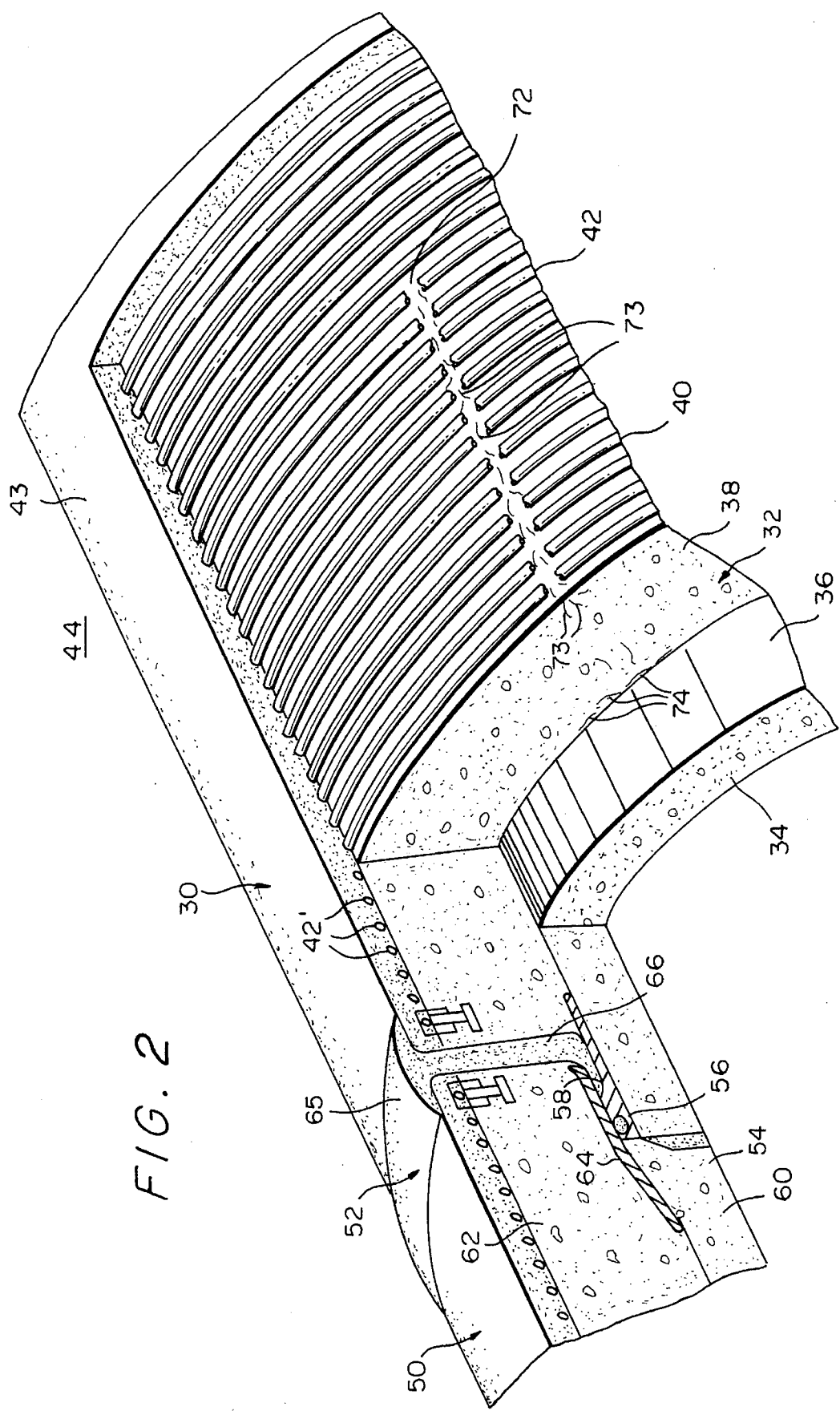
FIG. 2 is a perspective, similar to FIG. 1, of a pipe having a second configuration.

FIG. 2 discloses a second embodiment of PCCP pipe 30 which is configured differently from the pipe 10 of FIG. 1 in that a steel cylinder 36 is embedded in the concrete. The pipe 30 includes a core concrete layer 32 a concrete liner layer 34, a steel membrane 36 and a core layer 38. Disposed over the core layer 38 is the strand layer 40 comprised of steel reinforcing "wire" 42 wound around the core layer. The steel reinforcing wire 42 is in turn enveloped by a mortar layer 43 which interfaces with the soil 44 sounding the pipe 30 and prevents the surrounding soil environment from coming into contact with and corroding the steel wire 42.

In the embodiment of FIG. 2, the pipe 30 couples with a second pipe 50 of a similar configuration with a joint 52. At the joint 52, the concrete core 38 is stepped back from the liner layer 34 to form an annular lip 54 which has an annular gasket 56 thereon. The pipe 50 has an opposed, complementing step 58 formed by indenting its concrete liner layer 60 with respect to its concrete core layer 62. A gasket 64 is positioned on the projecting portion of the concrete core 62 and engages the gasket layer 56 on the projecting annular lip 54 of the pipe 30. An annular bead 65 of mortar with a rib portion 66 extends between the concrete cores 62 and 38 of the respective pipes 30 and 50 and seals the gap at the pipe joint 52.

In both the pipes 10 and 30, the reinforcing wires 16 and 42, respectively, place the inner concrete layers 12 and 32, respectively, in circumferential compression enabling the pipes to withstand water pressure within the pipe on the order of 200 pounds per square inch. Without the prestressed steel reinforcing wire 16 or 42, the pressure within the pipes 30 and 10 forces the steel cylinder apart and water begins to seep through the walls of the pipe, resulting in very rapid destruction of the pipe.

When the first wire turns 16 or 42 break, as is illustrated by areas 70 and 72, there is immediate localized difference in compression between the portions of the concrete cores 12 or 38 compressed by the wires and the portions of the concrete cores which have had their compression relieved by rupture of the wires. Over time, the resulting tension between these adjacent portions of the concrete cores 12 and 38 reach a level that exceeds the physical strength of the concrete cores 12 and 38, initiating microcracking 73 of the cores. With time, these cracks grow.

As the pipes 10 and 30 deteriorate adjacent the ruptures 70 and 72, the mortar 18 and 43 delaminates from the wires 16 and 12, respectively. More of the wire turns 16 and 42 become exposed to ground water and eventually additional wire breaks occur which in turn increases the number and rate of cracks in the concrete cores 12 and 38.

As the delamination continues, groups of wire turns 16 and 42 fail and the extent of cracking of the concrete cores 12 and 38 increase in severity. Since the cylindrical steel membrane 36 is relatively thin, it will rupture when not sufficiently supported by the concrete core 38. Rupture is accelerated by voids 74 occurring in the concrete core 38 and concrete layer 34.

Normally, sudden bursting failure occurs when about one hundred of the mid-pipe wire turns 16 or 42 are broken. If the deterioration occurs near the pipe joints 22 and 52, total failure of the pipes occur sooner because rupture of fewer, approximately 40, wire turns 16' or 42', will result in failure.

Figure 3:
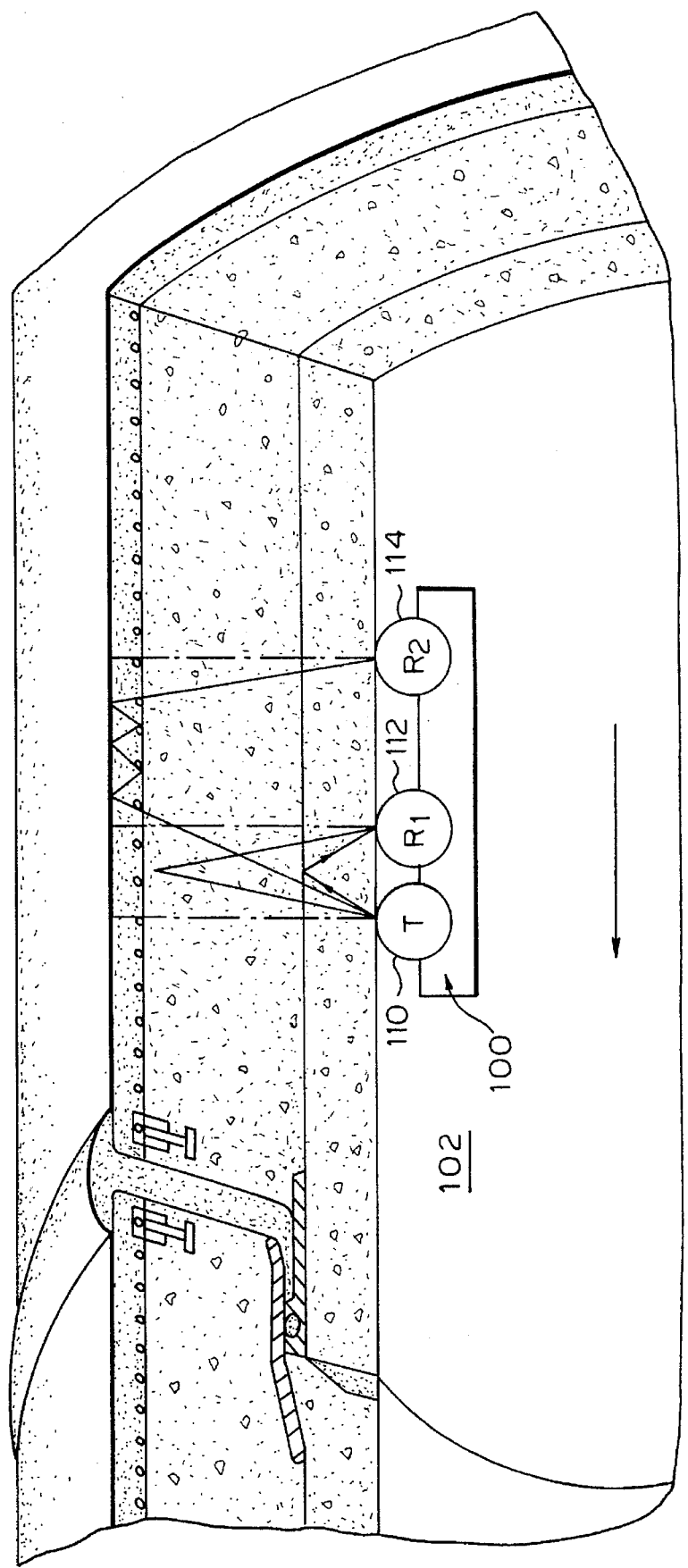
FIG. 3 is a perspective view, partially in section, of the pipe of FIG. 2 being monitored by surveying apparatus.

Referring now to FIG. 3, there is schematically shown apparatus 100 configured to perform the method of the present invention. The apparatus 100 may have a number of configurations. At the present time, the apparatus 100 may be configured as a simple manual device which is held against the surface 102 of the pipe 30 or it may be a wheeled sensing vehicle which is radially biased to engage the surface 102 for both rotational and axial movement with respect to the wall 102. The apparatus 100 is shown in direct contact with the surface 102 of the wall, but it is within the contemplation of this invention to have an apparatus which travels in the water of a full pipe 30, both transmitting and receiving signals through the water and pipe wall so that the pipe need not be emptied of water in order to be evaluated.

The survey apparatus 100 includes an impact source 110 and at least one sensor 112. Additional sensors such as the sensor 114 may also be employed. The impact source 110 may be a single impact from a small steel sphere discharged at a selected velocity against the wall 102 to generate sonic waves or may be an ultrasonic generator which impacts on the surface of the wall 102 with an ultrasonic signal. In either case, the generated signals will have the characteristics set forth in FIGS. 4–7.

Figure 4:
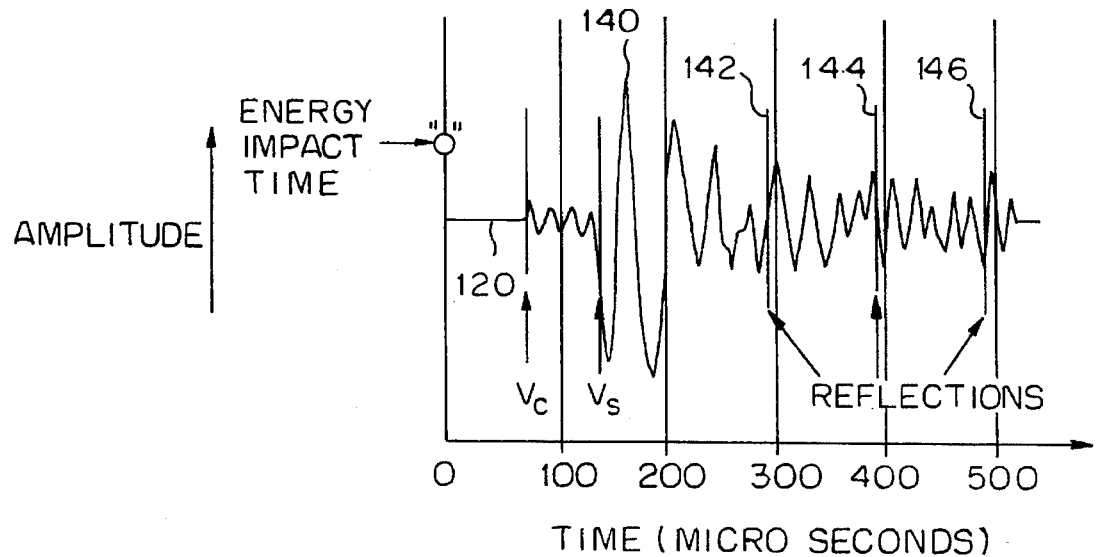
FIG. 4 is a graph plotting amplitude as a function of for a sound wave propagating through a prestressed concrete cylinder pipe (PCCP) in good condition.
Figure 5:
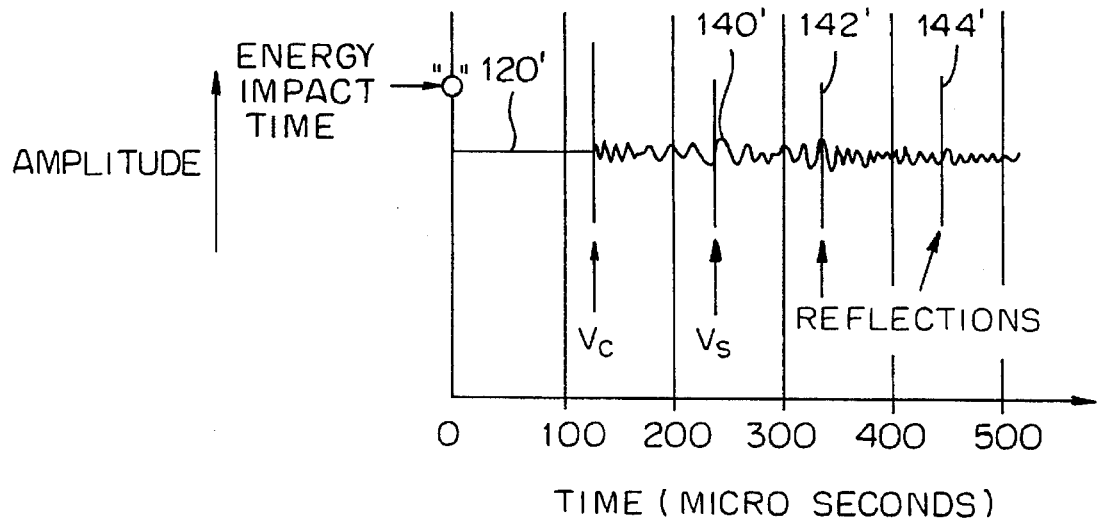
FIG. 5 is a graph similar to FIG. 4 but showing propagation of a sound wave in a PCCP pipe in poor condition.

Referring now to FIGS. 4 and 5, the amplitudes of a compression wave and shear wave are plotted as a function of time for a concrete pipe 30 which is in good condition.

In FIG. 4, the sensor 112 is displaced one foot from the impact source 110. The impact occurs at time "0". The signal 120 detected by the sensor 112 is flat for about 70 microseconds. At 70 microseconds, the compressional signal $V_c$ wave is detected. At about 130 microseconds, the shear wave signal $V_s$ is detected, resulting in an abrupt increase in amplitude 140 of the signal. The combined amplitude of the compressional and shear waves then decays with reflections occurring at points 142, 144 and 146. In pipes 30 having good concrete, the velocity of the compressional wave is about 13500 inches per second and the velocity of the shear wave is about 8000 ft. per second, these velocities being computed for waves moving in the axial direction with respect to the pipe. The resulting compressional wave and shear wave characteristics displayed in the graph of FIG. 4 for pipes having good concrete are then used in a comparison to determine when a pipe is in poor condition by comparing the signal of FIG. 5 to the signal FIG. 4.

Referring now to FIG. 5, it is readily apparent that the signal 120' differs from the signal 120. If the concrete of the pipe 30 is decompressed because the wire turns 42 are ruptured, then the compressional wave velocity is reduced from about 13,500 ft. per second to about 8,000 ft. per second and shear wave velocity is reduced from about 8,000 ft. per second to about 4,200 ft. per second. Since the compressional wave velocity is reduced, the compression wave signal $V_c$ is detected at about 130 microseconds rather than at about 70 microseconds. Shear wave velocity is also reduced so that the shear wave signal $V_s$ identified by peak 140' is detected at about 230 microseconds rather than 130 microseconds. Moreover, since the compressional and shear wave velocities are reduced in a pipe 30 of poor condition, the reflections 142' and 144' with the decompressed concrete occur later than the reflections 142 and 144 in the compressed concrete of a sound pipe. The number of detectable reflections is also reduced so that there may be insufficient signal strength to generate a detectable third reflection 146.

In addition to delayed times of detection, it is also readily apparent that the signal peak 140' indicating detection of the shear wave in the degraded pipe is substantially less than the peak 140 indicating detection of the shear wave in the sound pipe.

By making comparisons of detection times for compressional and shear waves as well as comparisons of shear wave amplitudes, an evaluation as to the condition of the pipe 30 may be readily made.

Figure 6:
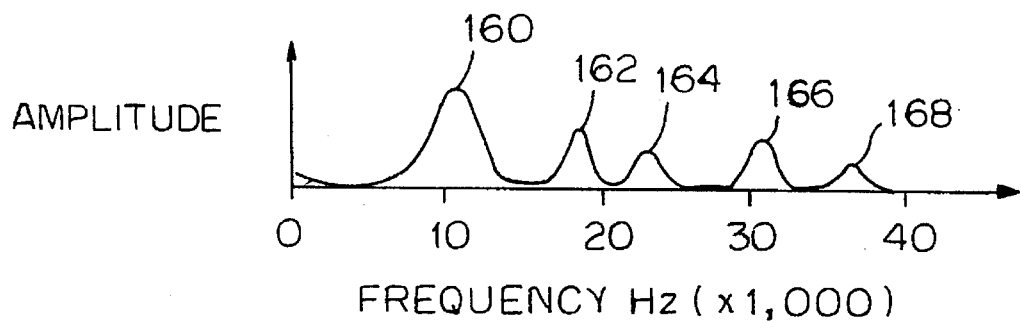
FIG. 6 is a graph plotting amplitude as a function of frequency wave propagating in a PCCP pipe in good condition.
Figure 7:
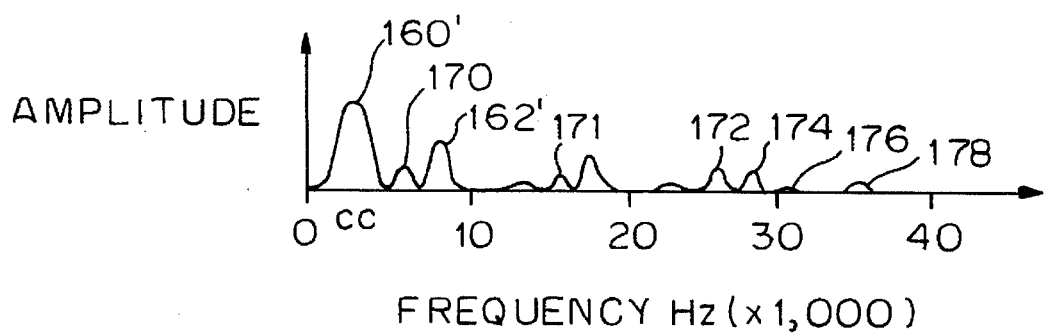
FIG. 7 is a graph plotting amplitude as a function of frequency for a sound wave propagating in a PCCP pipe in poor condition.

Referring now to FIGS. 6 and 7 where the amplitude of detected signals as a function of frequency is illustrated, it is seen that the amplitude/frequency wave forms for poor concrete (FIG. 7) differ substantially from the amplitude/frequency wave form characteristics for the concrete of a sound pipe. The reasons for this difference become apparent when considering the schematic illustration of FIG. 8 directed to the pipe 30 of FIGS. 2 and 3.

Figure 8:
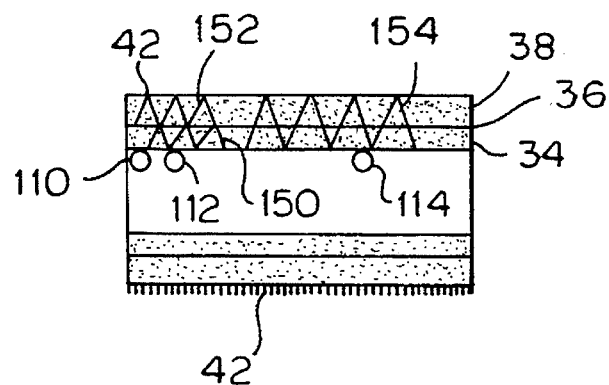
FIG. 8 is a schematic, side elevation of a portion of the pipe of FIG. 2 showing sonic or ultrasonic wave forms propagating in different layers of concrete.

Referring now to FIG. 8, it is seen that the concrete liner layer 34 propagates a first sound wave 150 and the concrete core 38 propagates a second sound wave 152. The first and second sound waves 150 and 152 subsequently combine to produce a composite wave 154 which traverses the steel membrane 36.

As is seen in FIG. 6, when monitoring the frequency domain for concrete pipe in good condition, the composite wave 154 resonates at about 10,000 Hz as is evidenced by the wave peak 160. The sound wave 152 in the concrete core 38 resonates at about 18000 Hz as is evidenced by the peak 162, while the first harmonic of the composite wave 154 resonates at about 23000 Hz as is evidenced by the peak 164. The wave 150 in the concrete liner layer 34 resonates at about 31,000 Hz as is evidenced by the peak 166, while the second harmonic of the composite wave 154 resonates at about 37,000 Hz as is evidenced by the peak 168. For concrete in good condition with the compressional wave velocity of about 13,500 ft. per second and a shear wave velocity of about 8000 ft. per second, there is a definite frequency domain pattern as compared to the frequency domain pattern for decompressed concrete showing in FIG. 7 which indicates the likelihood of a future catastrophic break.

As is seen in FIG. 7, resonance of the wave 154 occurs at about 6000 Hz as is evidenced by the signal wave peak 170. The resonance of the wave 152 in the core sample 38 occurs at about 8,0000 Hz as evidenced by peak 162'. The peak at 160' represents the resonant period of a weak, cracked zone of concrete due to delamination and cracking. This is similar to a "drum head" effect used for detecting delaminated concrete by human ear detection of the signal from a chain drag used in highway bridge deck evaluation. The remaining peaks 171–178 are further evidence of cracking where local zones have their own resonant frequencies and in addition cause destructive and constructive interference of the traveling stress waves. These peaks are of relatively low amplitude and are more numerous than the peaks of FIG. 6. Accordingly, by comparing the frequency domains for a pipe being evaluated (FIG. 7) with the frequency domain of the pipe known to be in good condition (FIG. 6), one can detect if wire turns 42 are ruptured, resulting in decompressed or otherwise damaged concrete.

Clearly, by comparing the time and amplitude parameters of FIG. 5 with respect to those of FIG. 4 and comparing the frequency domain characteristics of FIG. 7 to that of FIG. 6, a composite picture of a portion of the pipe 30 occurs which helps the water supply utility evaluate the pipe 30 and decide when to replace the pipe 30. Since a main includes hundreds of sections of pipe 30, a maintenance program can be initiated for replacing the badly degraded pipe sections first and then perhaps replacing other sections after further monitoring. The signals of FIGS. 4–7 of each pipe section can be stored for subsequent comparisons to determine if degradation is accelerating with time.

By employing the method of the present invention, early detection of potential breaks in water mains is possible, thus allowing sections of water main pipe which are in poor condition to be replaced before rupture. A program employing this method can thus save the water utility or water company millions of dollars while minimizing the disruption and property damage occasioned by catastrophic water main breaks.

Sonic/ultrasonic stress wave measurements can detect micro-cracking of pipe concrete which is not visible as well as visible macro-cracking. The process of concrete deterioration initiates from micro-cracks which, with continued fatigue from whatever cause, coalesce and become macro-cracks that progress toward failure through the horizontal crack development which precedes imminent failure. Since initial microcracking occurs years before failure, a system employing the principals of the present invention is useful as an early warning system for pipe management.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of evaluating the condition of a prestressed concrete cylinder pipe, wherein the pipe comprises at least an inner concrete layer having an inner wall surface, a prestressed strand layer disposed around the inner concrete layer and an outer mortar layer disposed over the prestressed strand layer, the method comprising the steps of:

a) determining the frequency domain characteristics and the velocity characteristics of reflected compressional and shear sound waves generated from an impact signal applied to the inner wall surface of the inner concrete layer of a pipe known to be in good condition;

b) determining the frequency domain characteristics and the velocity characteristics of reflected compressional and shear sound waves generated by an identical impact signal applied to the inner wall surface of the inner concrete layer of the pipe being evaluated; and c) comparing the characteristics detected in step b) to the characteristics detected in step a) to determine if the prestressed strand layer has ruptured.

2. The method of claim 1, wherein the velocity characteristics being determined include compressional wave velocity and shear wave velocity.

3. The method of claim 2, wherein the frequency domain characteristics are monitored to detect a drum head effect indicating that a prestressed strand layer has ruptured.

4. The method of claim 3, wherein the amplitude of the compressional wave and the amplitude of the shear wave are also determined in steps a) and b) and compared in step c) to determine if the strand layer is ruptured.

5. The method of claim 1, wherein the inner layer of concrete of both the pipe known to be in good condition and the pipe being evaluated each includes a core layer and a liner layer with a steel membrane disposed therebetween and wherein the frequency domain characteristics are monitored for lower frequencies and additional peaks occurring in step b) as compared to frequencies and peaks occurring in step a).

6. The method of claim 5, wherein, if the frequency domain characteristics determined in step b) have lower frequency resonances for the core layers and inner layers individually and for the core layers and liner layers combined than the frequency resonances detected in step a) when compared in step c), then the strand layer is ruptured.

7. The method of claim 1, wherein, if the compressional and shear velocities determined in step b) are less than the compressional and shear velocities determined in step a) when compared in step c), the strand layer is ruptured.

8. The method of claim 1, wherein the prestressed strand layer is coiled steel wire.

9. The method of claim 1, wherein the velocity of the compressional wave is about 13,500 inches/sec and the velocity of the shear wave is about 8000 inches/sec if the strand layer is unruptured and about 8000 inches/sec and 4200 inches/sec, respectively, if the strand layer is ruptured.

10. The method of claim 1, wherein the impact signal is a sonic signal.

11. The method of claim 1, wherein the impact signal is an ultrasonic signal.

* * * * *